United States Patent [19]

Tanaka et al.

[11] 4,275,011

[45] Jun. 23, 1981

[54] METHOD OF PRODUCING IMPROVED GLYCERIDE BY LIPASE

[75] Inventors: Takashi Tanaka; Eiji Ono, both of Kawasaki; Koichi Takinami, Yokohama, all of Japan

[73] Assignee: Ajinomoto Company, Incorporated, Tokyo, Japan

[21] Appl. No.: 105,713

[22] Filed: Dec. 20, 1979

[30] Foreign Application Priority Data

Dec. 20, 1978 [JP] Japan ............................... 53-159517

[51] Int. Cl.$^{3}$ ........................... C11C 3/02; C12P 7/64

[52] U.S. Cl. ................................. 260/410.7; 435/134; 435/917; 435/921; 435/937

[58] Field of Search ..................... 260/410.7; 435/134, 435/917, 921, 937

[56] References Cited

U.S. PATENT DOCUMENTS

| | | | |
|---|---|---|---|
| 4,032,405 | 6/1977 | Tatsumi et al. | 435/134 |
| 4,056,442 | 11/1977 | Huang et al. | 435/921 |

OTHER PUBLICATIONS

Vogel et al., Chem. Absts., vol. 63, No. 4771h, (1965).

*Primary Examiner*—John F. Niebling

*Attorney, Agent, or Firm*—Oblon, Fisher, Spivak, McClelland & Maier

[57] ABSTRACT

A glyceride product is prepared by interesterifying a glyceride mixture in the presence of a lipase as a catalyst with a dihydric alcohol, a trihydric alcohol, or mixture thereof, said glyceride mixture being composed of at least two different glycerides or at least one glyceride and at least one fatty acid.

9 Claims, No Drawings

METHOD OF PRODUCING IMPROVED GLYCERIDE BY LIPASE

BACKGROUND OF THE INVENTION

1. Field of the Invention

The present invention relates to a method of producing an improved glyceride product by interesterification with lipase.

2. Description of the Prior Art

Interesterification and hydrogenation are techniques which have been useful in the preparation of glyceride products for use in the manufacture of butter and margarine. In the conventional interesterification reaction, interesterification is conducted in the presence of a catalyst such as sodium, sodium methylate, or the like. However, the conventional reaction is not selective with respect to esterification of a fatty acid substrate at a reactive position with glycerine. On the other hand, an interesterification process conducted in the presence of lipase as a catalyst (Japanese Published Unexamined Patent Application No. 104506/1977) is know, however, this process requires the presence of water to activate the lipase. The presence of water causes hydrolysis of interesterified glycerides with resultant decreases in yield of the glyceride product. Therefore, a need continues to exist for a method of improving the yield of glyceride products by an interesterification reaction.

SUMMARY OF THE INVENTION

Accordingly, one object of the present invention is to improve the yield of a glyceride product by interesterification of a glyceride mixture.

Another object of the present invention is to improve the quality of natural oils and fats by selective interesterification.

Briefly, these objects and other objects of the invention as hereinafter will become more readily apparent can be attained by providing a method of producing an improved glyceride product in a reaction which employs lipase as a catalyst by interesterifying a glyceride mixture in the presence of a lipase as a catalyst with a dihydric alcohol, a trihydric alcohol or a mixture thereof, said glyceride mixture being composed of at least two different glycerides, or at least one glyceride and at least one fatty acid.

DETAILED DESCRIPTION OF THE PREFERRED EMBODIMENTS

The interesterification reaction of the present invention involving a glyceride mixture as the starting material is conducted in a medium in which there is a substantial absence of water. Suitable glyceride mixtures which may be used as starting materials in the present invention include animal oils and fats, vegetable oils and fats, and synthetic glycerides. Examples of vegetable oils and fats include palm oil and fat, soybean oil, rapeseed oil, olive oil, coconut oil, corn oil, cottonseed oil, safflower oil and the like. Examples of animal oils and fats include lard oil, tallow, fish oil, whale oil and the like. Examples of synthetic glycerides include trilaurin, tristearin, triolein and the like.

Fatty acids consist of a single carboxyl group attached to the end of a straight hydrocarbon chain, and the number of carbon atoms in the hydrocarbon chain ranges from 8 to 20. Suitable saturated fatty acids and unsaturated fatty acids which can be used in the present process include, for example, palmitic acid, stearic acid, oleic acid, linoleic acid and the like.

In the process of the present invention the glyceride mixture starting material contains one part of a raw glyceride mixture per 0.25∼4 parts of fatty acid component and/or other glyceride component.

Suitable lipase enzymes which can be used in the present process include those produced from microorganisms such as *Rhizopus japonicus, Aspergillus niger, Candida cylindracea, Geotrichum candidum* and the like. Lipases produced by thermophiles such as *Humicola lanuginosa* and *Thermomyces ibadanensis* are more preferred. Some of these lipases are commercially available, and such lipases can be preferably used in the present invention. The amount of lipase employed in the reaction depends on the kind of glyceride to be produced, the reaction conditions, and the stability of the lipase used. In case of commercial lipase, a suitable amount which is used in the present process ranges from 0.025 to 5 weight % based on the raw glyceride mixture, which is equivalent to from 5 to 5000 units/g oil.

The dihydric alcohol and trihydric alcohol components of the present reaction mixture by definition consist of two and three hydroxyl groups attached to a hydrocarbon chain, respectively. Suitable examples of dihydric alcohols and trihydric alcohols include ethylene glycol, propylene glycol, glycerine and the like. Dihydric alcohols and trihydric alcohols can be used together as starting materials in the present process, and the amount of alcohol used in the reaction is more than 0.1 weight % based on the raw glyceride mixture, preferably from 0.1 to 10 weight %.

The activity of the particular lipase enzyme used can be stimulated when the lipase is adsorbed on a carrier. The carrier used in the present invention should be a material which is insoluble in the reaction mixture, which is capable of adsorbing the enzyme on its surface, and which does not adversely affect the activity of the lipase. Suitable carriers include Celite, active carbon, cellulose, ion-exchange resin, glass fiber, glass beads, silica-gel, florisil, calcium carbonate, saccharide, alumina and the like. Usually the carrier is immersed in glycerine prior to enzyme adsorption. The amount of carrier employed in the present invention preferably ranges from 2.5% to 25% of the raw glyceride.

The temperature at which the interesterification reaction is conducted is determined by the activity of lipase. The preferred range is from 20° C. to 80° C., more preferably from 20° C. to 50° C. While side reactions do not occur at low temperatures, the reaction, however is very slow. In the range of from 20° C. to 35° C. a triglyceride which is mainly composed of palmitic acid is produced. In the range of from 35° C. to 80° C. a triglyceride which is mainly composed of stearic acid is produced. A suitable range of time for the interesterification reaction is 1 day to 3 days.

Since the reaction mixture is not very fluid because of the low reaction temperature employed, an inert organic solvent which dissolves the glyceride and fatty acid starting materials can be added to the reaction mixture to increase the fluidity of the same. Suitable examples of inert organic solvents include petroleum benzine, petroleum ether, n-hexane, and the like. The amount of inert organic solvent employed in the present invention preferably ranges from one part to 10 parts of raw glyceride and the addition of the inert organic solvent to the reaction mixture promotes the same.

In order to avoid the contamination of the reaction mixture with water the reaction is preferably performed in a closed vessel. The presence of water in the reaction mixture reduces the efficiency of the interesterification reaction. Accordingly, prior to reaction, the water present in the raw glyceride mixture, fatty acids, dihydric alcohol and trihydric alcohol, the inert organic solvents, and the carrier should be removed. Because the present reaction is performed under conditions in which water is essentially absent, the yield of the exchanged glycerine product obtained is greater by 5% to 10% in comparison to the cases when significant quantities of water are present in the reaction mixture.

The reaction mixture obtained in the present process contains fatty acids, and small amounts of mono-glyceride, di-glyceride, and other impurities. These impurities can be removed by the usual separation and refining processes such as the liquid-liquid extraction, alkaline neutralization and distillation. If required, the glycerine product obtained is subjected to solvent separation or hydrogenation.

One of the merits of the present invention is that interesterification promoted by lipase is selective, while chemical esterification is not selective. For example, Rhizopus lipase reacts selectively with fatty acids at the 1 and 3 positions of glycerine and does not react at the 2-position of glycerine. On the other hand, Geotrichum lipase reacts selectively with the fatty acids which have a double bond at the 9-position such as oleic acid and linoleic acid. Then, depending upon the raw glyceride and fatty acid selected, various kinds of glycerides can be produced. For example, valuable cocoa butter can be prepared from palm oil which is available at a reasonable price.

In order to produce a triglyceride which resembles cocoa butter, it is possible to produce a glyceride mixture which resembles natural oils and fats by controlling the time at which the fatty acid is added. In this case side reactions are not a significant problem.

Having generally described this invention, a further understanding can be obtained by reference to certain specific examples which are provided herein for purposes of illustration only and are not intended to be limiting unless otherwise specified.

EXAMPLE 1

A 10 g amount of olive oil, 10 g of stearic acid, 1 g of Celite, the amount of glycerin shown in Table I, 40 mg of the commercial lipase of *Rhizopus delemar* produced by Seikagaku Kogyo Co., Ltd. Japan, and 40 ml of petroleum benzine were mixed, and the mixture was stirred in a closed container for 3 days at 40° C. For comparative purposes the reaction was performed by substituting water for glycerin. After the reaction was terminated, the precipitate, a mixture of Celite, glycerin, and lipase, was separated by filtration, and washed with 40 ml of petroleum benzine. The above filtrates(oil phase) were mixed to petroleum benzine and evaporated to dryness. The dried glyceride product obtained was purified by florisil column chromatography using ethyl ether (20%) and n-hexane (80%) as the developing solvent. The purified glyceride was subjected to preparative thin-layer chromatography (TLC). The triglyceride content was measured by the TLC technique. The triglyceride fractions were collected, and the yield of triglyceride was measured. The fatty acid content in the obtained triglyceride was measured by gas chromatography according to the technique described in: "Official and Tentative Methods of the Japan Oil Chemists' Society" (2.4.20.2-77). The results are shown in Table I.

TABLE I

| | The Present Invention (glycerin) | | Comparison (water) | |
|---|---|---|---|---|
| Glycerine added (g) | Stearic acid cont. in Triglyceride (%) | Yield of Triglyceride (%) | Stearic acid cont. in triglyceride (%) | Yield of triglyceride (%) |
| 0 | 3.2 | 96.5 | 3.2 | 96.5 |
| 0.01 | 4.1 | | 2.6 | |
| 0.02 | 11.4 | | 4.9 | |
| 0.05 | 36.5 | 87.0 | 36.2 | 77.0 |
| 0.1 | 41.2 | 77.5 | 39.0 | 68.7 |
| 0.2 | 40.2 | | 39.1 | |
| 0.5 | 39.5 | 61.1 | 39.3 | 50.2 |

EXAMPLE 2

A 10 g amount of olive oil (containing 2.9% stearic acid) and 10 g of stearic acid, were mixed with 40 ml of petroleum benzine, 20 mg of the commercial lipase of *Rhizopus delemar,* 0.05 ml of glycerine and 1.0 g of the carrier listed in Table 2. Each mixture was stirred in a closed container for 3 days at 30° C.

The triglyceride was separated from the resultant reaction mixture according to the manner of Example 1. The stearic acid content in the triglyceride was measured by gas chromatography.

As shown in Table 2, the interesterification reaction was promoted by adding the carrier.

TABLE 2

| Carrier used | Stearic acid cont. in triglyceride (%) |
|---|---|
| none | 10.5 |
| Celite | 28.8 |
| $CaCO_3$ | 30.3 |
| Quartz sand | 27.9 |
| Glucose | 27.9 |
| Alumina | 27.6 |
| Silicic acid | 25.5 |
| Active carbon | 26.4 |
| $K_2CO_3$ | 22.7 |
| Cellulose | 11.5 |
| Florisil | 17.3 |

EXAMPLE 3

A 10 g amount of safflower oil (containing 2.8% of stearic acid) and 10 g of stearic acid, were mixed with 40 mg of the commercial lipase of *Rhizopus delemar,* 0.1 ml of glycerin, 1.0 g of Celite, and the amount of n-hexane shown in Table 3. The mixture was stirred in a closed container for 3 days at 30° C. A triglyceride product was separated from the resultant reaction mixture by the manner described in Example 1. The stearic acid content of the triglyceride was measured by gas chromatography.

The results are shown in Table 3.

TABLE 3

| n-Hexane added (ml) | Stearic acid cont. in triglyceride (%) |
|---|---|
| 0 | 16.1 |
| 10 | 23.0 |
| 20 | 26.1 |
| 40 | 31.9 |

EXAMPLE 4

A 10 g amount of olive oil and 10 g of stearic acid were mixed with 40 mg of the commercial lipase of *Rhizopus delemar*, the amount of ethylene glycol or propylene glycol shown in Table 4, 1.0 g of Celite, and 40 ml of n-hexane. The mixture was stirred in a closed vessel for 3 days at 20° C. or 30° C. The triglyceride product was separated from the resultant reaction mixture by the manner described in Example 1. The stearic acid content of the triglyceride was measured by gas chromatography.

The results are shown in Table 4.

TABLE 4

| Glycol used(g) | Stearic acid cont. in triglyceride (%) Ethylene glycol (temo. 30° C.) | Propylene glycol (temp. 20° C.) |
|---|---|---|
| 0 | 3.3 | 3.4 |
| 0.05 | 29.1 | 10.2 |
| 0.10 | 32.3 | 11.5 |

EXAMPLE 5

A 0.1 g amount of glycerin and 1.0 g of Celite were mixed with 10 g of coconut oil, olive oil and 60 mg of the commercial lipase of *Candida cylindracea* produced by SIGMA CHEMICAL COMPANY. The mixture was stirred in a closed container for 3 days at 30° C. The resultant reaction mixture was centrifuged, the oil phase was separated by decantation, and the insoluble matter was washed with 40 ml of petroleum benzine. The washed liquid (petroleum benzine) was added to the oil phase, and the solvents in the oil phase were removed by reduced pressure distillation. The triglyceride content of the product was determined using a preparative silica-gel thin layer plate. The yield of triglyceride was 81%. The triglyceride was fractionated by gas chromatography in accordance with the carbon number of the triglyceride.

The results are shown in Table 5.

TABLE 5

| Carbon number of triglyceride* | Content of triglyceride (%) Before the reaction | After the reaction |
|---|---|---|
| 26~38 | 32.1 | 17.2 |
| 40~48 | 10.5 | 58.7 |
| 50~56 | 57.4 | 24.1 |

*The carbon number of glycerine was not counted.

The results show that the reaction is selective.

EXAMPLE 6

A 10 g amount of oleic safflower oil (containing 5.7% of palmitic acid) and 10 g of palmitic acid were mixed with 20 mg of each one of the commercial lipases shown in Table 6, 0.1 g of glycerine, 1.0 g of powdered calcium carbonate, and 40 ml of petroleum benzine. The mixtures were stirred in a closed container for 3 days at 40° C. The triglyceride product was separated from the resultant reaction mixture by the manner described in Example 1. The palmitic acid content of the triglyceride was measured by gas chromatography. The results are shown in Table 6.

TABLE 6

| Lipase Source | Producer | Palmitic acid cont. in triglyceride (%) |
|---|---|---|
| *Rhizopus delemar* | SEIKAGKU KOGYO CO., LTD. | 43.3 |
| *Phizopus japonicus* | OSAKA SAIKIN LABORATORIES CO., LTD. | 43.7 |
| *Asperigillus niger* | AMANO SEIYAKU CO., LTD. | 40.2 |
| *Candida cylindracea* | MEITO SANGO CO., LTD. | 46.8 |
| *Geotrichum candidum* | SEIKAGAKU KOGYO CO., LTD. | 37.6 |
| *Alcaligenes sp.* | MEITO SANGYO CO., LTD. | 38.5 |
| *Pancreatin lipase* | SIGMA CHEMICAL COMPANY | 40.0 |

EXAMPLE 7

A 10 g amount of natural oil shown in Table 7 and 10 g of stearic acid were mixed with 40 mg of the commercial lipase of *Rhizopus delemar*, 40 ml of n-hexane, 0.1 g of glycerin, and 1.0 g of Celite. The mixture was stirred in a closed container for 3 days at 30° C. The triglyceride product was separated from the resultant reaction mixture by the manner described in Example 1. The stearic acid content of the triglyceride was measured by gas chromatography.

The results are shown in Table 7.

TABLE 7

| Raw oil used | Stearic acid cont. (%) in raw triglyceride | in reactant triglyceride |
|---|---|---|
| Fractionated palm oil (liquid phase) | 6.3 | 34.9 |
| Cocunut oil | 3.7 | 37.5 |
| Oleic safflower oil | 2.2 | 36.9 |
| Olive oil | 2.9 | 31.8 |
| Soybean oil | 4.1 | 33.5 |
| Rapeseed oil | 2.3 | 31.1 |
| Linseed oil | 3.0 | 32.3 |
| Safflower oil | 2.8 | 31.7 |
| Rice oil | 1.8 | 28.7 |
| Camellia oil | 2.1 | 31.6 |
| Peanut oil | 4.9 | 33.0 |
| Sesame oil | 5.3 | 34.5 |
| Sunflower oil | 3.2 | 34.3 |
| Cottonseed oil | 3.3 | 32.2 |
| Corn oil | 2.8 | 35.4 |
| Tallow | 24.5 | 43.5 |
| Lard | 15.3 | 41.2 |

EXAMPLE 8

A 1.0 g amount of one of the synthetic triglycerides shown in Table 8 and 1.0 g of a fatty acid were mixed with 4 mg of the commercial lipase of *Rhizopus delemar*, 4.0 ml of petroleum benzine, 0.01 g of glycerine, and 0.1 g of Celite. The mixture was stirred in a closed container for 3 days at 30° C.

The triglyceride was separated from the resultant reaction mixture by the manner described in Example 1. The fatty acid contents of the triglyceride were measured by gas chromatography.

The results are shown in Table 8.

TABLE 8

| Synthetic Trigly-ceride | Fatty acid | Fatty acid* cont. in triglyceride (mol %) | | | | | |
|---|---|---|---|---|---|---|---|
| | | $C_{12:0}$ | $C_{14:0}$ | $C_{16:0}$ | $C_{18:0}$ | $C_{18:1}$ | $C_{18:2}$ |
| Trilaurin | — | 98.1 | 1.1 | — | | | |
| Trilaurin | Stearic acid | 60.5 | — | 0.7 | 31.9 | | 6.9 |
| Trimyristin | — | 1.3 | 97.8 | 0.9 | | | |
| Trimyristin | Stearic acid | | 56.0 | 0.5 | 43.1 | | 0.5 |
| Tripalmitin | — | | 2.1 | 90.5 | 7.4 | | |
| Tripalmitin | Stearic acid | | | 73.7 | 26.4 | | |
| Tristearin | — | | | 0.5 | 99.5 | | |
| Tristearin | Palmitic acid | | | 37.2 | 62.8 | | |
| Triolein | — | | | | 0.5 | 99.1 | 0.3 |
| Triolein | Stearic acid | | | 0.9 | 31.4 | 67.8 | |

*$C_{12:0}$ Lauric acid
*$C_{14:0}$ Myristic acid
$C_{16:0}$ Palmitic acid
*$C_{18:0}$ Stearic acid
*$C_{18:1}$ Oleic acid
*$C_{18:2}$ Linoleic acid

EXAMPLE 9

A 10 g amount of oleic safflower oil or 10 g of coconut oil, and 10 g of one of the fatty acids shown in Table 9 were mixed with 40 ml of petroleum benzine, 20 mg of the commercial lipase of *Rhizopus delemar,* 0.05 g of glycerine, and 1.0 g of Celite. The mixture was stirred in a closed container for 3 days at 34° C.

The triglyceride was separated from the resultant reaction mixture by the manner described in Example 1. The fatty acid content of the triglyceride was measured by gas chromatography.

The results are shown in Table 9 and Table 10.

TABLE 9

INTERESTERIFICATION OF OLEIC SAFFLOWER OIL

| Fatty acid | Fatty acid* cont. in triglyceride (mol %) | | | | | | |
|---|---|---|---|---|---|---|---|
| | $C_{10:0}$ | $C_{12:0}$ | $C_{14:0}$ | $C_{16:0}$ | $C_{18:0}$ | $C_{18:1}$ | $C_{18:2}$ |
| Capric acid | 20.9 | 0.4 | 3.8 | 2.1 | 0.9 | 56.5 | 15.1 |
| Lauric acid | 0.2 | 26.9 | 1.5 | 3.4 | 1.2 | 51.2 | 15.6 |
| Myristic acid | 0 | 0.3 | 28.5 | 3.3 | 1.1 | 52.8 | 13.9 |
| Palmitic acid | 0 | 0 | 0.1 | 28.3 | 1.6 | 56.1 | 14.2 |
| Stearic acid | 0 | 0 | 0 | 3.9 | 23.3 | 57.9 | 14.9 |
| (raw oil) | 0 | 0 | 0 | 5.7 | 1.9 | 74.3 | 18.1 |

*$C_{10:0}$ *Capric acid*

TABLE 10

INTERESTERIFICATION OF COCONUT OIL

| Fatty acid | Fatty acid cont. in triglyceride (mol %) | | | | | | |
|---|---|---|---|---|---|---|---|
| | $C_{10:0}$* | $C_{12:0}$ | $C_{14:0}$ | $C_{16:0}$ | $C_{18:0}$ | $C_{18:1}$ | $C_{18:2}$ |
| Oleic acid | 11.7 | 40.9 | 14.0 | 8.3 | 2.4 | 21.0 | 1.8 |
| Linoleic acid | 10.3 | 37.1 | 15.3 | 9.7 | 3.0 | 7.1 | 17.5 |
| (raw oil) | 14.2 | 38.9 | 17.9 | 10.3 | 3.7 | 8.3 | 6.6 |

*$C_{10:0}$ This symbol indicates a fatty acid mixture which includes capric acid, caprylic acid caproic acid, and butyric acid. (The carbon atom number is not larger than 10.)

EXAMPLE 10

A 10 g amount of oleic safflower oil and 10 g of palmitic acid were mixed with 40 ml of petroleum benzine, 40 mg of one of the commercial lipases shown in Table 11, 1.0 g of Celite, and 0.05 ml of glycerin. This mixture was stirred in a closed container for 3 days at 30° C. The resulting triglyceride product was separated from the resultant reaction mixture by the manner described in Example 1. The fatty acid content of the triglyceride product was measured by gas chromatography.

The results are shown in Table 11.

TABLE 11

| Lipase | Fatty acid cont. in triglyceride (mol %) | | | |
|---|---|---|---|---|
| | $C_{16:0}$ | $C_{18:0}$ | $C_{18:1}$ | $C_{18:2}$ |
| — | 6.2 | 2.2 | 75.5 | 17.0 |
| *Rhizopus delemar* | 40.1 | 0.8 | 48.4 | 21.1 |
| *Aspergillus niger* | 40.2 | 1.2 | 47.3 | 11.2 |
| *Candida cylindracea* | 47.0 | 2.0 | 42.2 | 9.1 |

The fatty acid content at the 2-position of the triglyceride product was analyzed by the method written in the "Yukagaku", vol. 20, page 284 (1971) published by the Japan Oil Chemists, Society.

The results are shown in Table 12.

TABLE 12

| Lipase | Fatty acid cont. in 2-position of triglyceride | | | |
|---|---|---|---|---|
| | $C_{16:0}$ | $C_{18:0}$ | $C_{18:1}$ | $C_{18:2}$ |
| — | 0.2 | 0.5 | 77.2 | 23.2 |
| *Rhizopus delemar* | 2.1 | 0.1 | 75.0 | 23.0 |
| *Asperigillus niger* | 14.1 | 0.1 | 67.8 | 18.2 |
| *Candida cylindracea* | 34.0 | 0.1 | 54.1 | 13.2 |

As shown in Table 12, when the lipase of *Rhizopus delemar* was used, palmitic acid reacted almost entirely at the 1 and 3 positions, and did not react at the 2-position. On the other hand, when the lipase from *Aspergillus niger* was used, about a tenth of the palmitic acid reacted at the 2-position. When the lipase from *Candida cylindracea* was used, the interesterification reaction was not selective.

EXAMPLE 11

A 0.1 ml amount of glycerine, 40 mg of the commercial lipase of *Rhizopus delemar,* and 5.0 ml of ethanol were added to 1.0 g of Celite, and the mixture was stirred sufficiently. Ethanol was removed under reduced pressure. The lipase adhered to the Celite carrier.

A 10 g amount of palm fractionated oil, 10 g of stearic acid, and 40 ml of petroleum benzine were mixed with the carrier, and the mixture was stirred in a closed container for 3 days at 30° C. The carrier was removed from the resultant reaction mixture by filtration and was washed with 40 ml of petroleum benzine. The washed solution was added to the oil phase, and petroleum benzine was removed under reduced pressure. Thereafter, with the molecular distillation of the fatty acid, monoglycerides, diglycerides, and the like were removed, and oil A was produced. (Yield: 89%).

A mixture of 10 g of oleic safflower oil, 5 g of palmitic acid, and 5 g of stearic acid, and a mixture of 10 g of olive oil, 10 g of palmitic acid, and 10 g of stearic acid were each treated by the process described above. Oil products B and C were respectively produced. (Yield: oil B; 88%, oil C; 90%).

The fatty acid contents in oil A, oil B and oil C are shown in Table 13.

TABLE 13

| Oil | Fatty acid cont. in triglyceride (mol %) | | | | Fatty acid cont. in 2-position of the triglyceride (mol %) | | | |
|---|---|---|---|---|---|---|---|---|
| | $C_{16:0}$ | $C_{18:0}$ | $C_{18:1}$ | $C_{18:2}$ | $C_{16:0}$ | $C_{18:0}$ | $C_{18:1}$ | $C_{18:2}$ |
| Raw palm oil | 38.9 | 6.0 | 33.7 | 11.8 | 15.8 | 0.5 | 64.1 | 19.7 |

TABLE 13-continued

| | Fatty acid cont. in triglyceride (mol %) | | | | Fatty acid cont. in 2-position of the triglyceride (mol %) | | | |
|---|---|---|---|---|---|---|---|---|
| Oil | $C_{16:0}$ | $C_{18:0}$ | $C_{18:1}$ | $C_{18:2}$ | $C_{16:0}$ | $C_{18:0}$ | $C_{18:1}$ | $C_{18:2}$ |
| Oil A | 25.2 | 34.9 | 31.5 | 8.5 | 11.4 | 0.5 | 71.1 | 17.0 |
| Raw oleic safflower oil | 5.7 | 1.1 | 76.2 | 16.8 | 0 | 0 | 77.3 | 22.7 |
| Oil B | 24.7 | 35.1 | 31.2 | 8.0 | 10.8 | 0 | 71.5 | 17.7 |
| Raw olive oil | 14.1 | 2.9 | 76.0 | 6.9 | 1.8 | 0 | 91.9 | 6.1 |
| Oil C | 27.1 | 32.3 | 39.0 | 1.7 | 7.3 | 6.5 | 81.6 | 4.6 |
| Natural cocoa butter | 24–30 | 30–38 | 30–39 | 2–4 | 4–16 | 3–8 | 70–84 | 6–9 |

The fatty acid content in the oils and the fatty acid contents in the 2-position of the triglyceride of oil A, oil B, and oil C resemble natural cocoa butter.

EXAMPLE 12

A 10 g amount of olive oil, and 20 g of stearic acid were mixed with 40 ml of n-hexane, 40 mg of the commercial lipase of *Rhizopus delemar,* 0.1 ml of glycerin, and 1 g of Celite. The mixture was stirred in a closed container at 30° C. A 10 g amount of palmitic acid was added 22 hours thereafter. The mixture was stirred in a closed container at 30° C. for 24 hours more. The resultant reaction mixture was subjected to filtration, and the remaining insoluble material was washed with 40 ml of n-hexene. The filtrate (oil phase) and n-hexene were mixed and evaporated to dryness under a reduced pressure at 45° C. (Oil A).

For comparative purposes the mixture to which 10 g of palmitic acid was added previously was treated in the same manner (Oil B).

The fatty acid content in the triglyceride and in the 2-position of the triglyceride was measured. The slip melting point was measured according to the method described in: "Official and Tentative Methods of the Japan Oil Chemists' Society" (2.3.4.2–71). The saturated triglyceride was analyzed by the peak area of the differential scanning calorimeter (DSC) pattern.

The results are shown in Table 14.

TABLE 14

| | Fatty acid cont. in triglyceride (mol %) | | | | Fatty acid cont. in 2-position of the triglyceride | | | |
|---|---|---|---|---|---|---|---|---|
| Oil | $C_{16:0}$ | $C_{18:0}$ | $C_{18:1}$ | $C_{18:2}$ | $C_{16:0}$ | $C_{18:0}$ | $C_{18:1}$ | $C_{18:2}$ |
| Oil A | 28.2 | 32.3 | 39.4 | 4.1 | 7.2 | 5.8 | 82.1 | 4.3 |
| Oil B | 35.1 | 19.4 | 46.7 | 4.9 | 13.2 | 7.8 | 62.2 | 4.9 |
| Natural cocoa butter | 27.1 | 33.4 | 36.2 | 4.3 | 6.0 | 4.0 | 83.0 | 7.0 |

| | Slip melting point (°C.) | Saturated triglyceride |
|---|---|---|
| Oil A | 30.1 | — |
| Oil B | 39.8 | ++ |
| Natural cocoa butter | 29.6 | — |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method of producing a glyceride, which comprises: interesterifying a glyceride mixture in the presence of a lipase as a catalyst and in the substantial absence of water with a dihydric alcohol, a trihydric alcohol, or a mixture thereof, said glyceride mixture being composed of at least two different glycerides or at least one glyceride and at least one fatty acid.

2. The method of claim 1, wherein said glyceride mixture is subjected to interesterification in the presence of the inert organic solvent.

3. The method of claim 1, wherein said glyceride mixture is subjected to interesterification in the presence of the carrier.

4. The method of claim 1, wherein said glyceride mixture is a mixture of glycerides, said mixture being selected from the group consisting of animal oils and fats, vegetable oils and fats, synthetic glyceride and mixtures thereof.

5. The method of claim 1 wherein said lipase is derived from a microorganism source.

6. The method of claim 1, wherein said glyceride mixture comprises one part of a raw glyceride mixture per 0.25~4 parts by wt. of said fatty acid, said at least one glyceride or a mixture thereof.

7. The method of claim 1, wherein said lipase is present in the reaction mixture in a concentration of 0.025 to 5 wt. % based on the amount of said raw glyceride mixture.

8. The method of claim 1, wherein said interesterificatiion reaction is conducted at a temperature of from 20° C. to 80° C.

9. The method of claim 1, wherein said dihydric alcohol is ethylene glycol or propylene glycol and said trihydric alcohol is glycerine.

* * * * *